United States Patent [19]

Frangatos

[11] 4,193,883
[45] Mar. 18, 1980

[54] LUBRICANT COMPOSITIONS

[75] Inventor: Gerassimos Frangatos, Cherry Hill, N.J.

[73] Assignee: Mobil Oil Corporation, New York, N.Y.

[21] Appl. No.: 887,397

[22] Filed: Mar. 16, 1978

[51] Int. Cl.$^2$ .............................................. C10M 1/10
[52] U.S. Cl. .............................. 252/49.9; 252/51.5 A; 252/400 A; 260/326.5 F; 260/326.5 FM; 260/927 R
[58] Field of Search ........................ 252/49.9, 51.5 A; 260/326.5 F, 326.5 FM, 927 R

[56] References Cited

U.S. PATENT DOCUMENTS

| 3,306,908 | 2/1967 | LeSuer | 260/326.5 F X |
| 3,325,567 | 6/1967 | LeSuer | 260/952 X |
| 3,663,439 | 5/1972 | Frangatos | 252/49.9 |
| 3,697,499 | 10/1972 | Myers | 252/48.8 X |
| 3,715,311 | 2/1973 | Brannen | 252/49.8 |
| 3,723,460 | 3/1973 | Brannen et al. | 252/49.9 X |
| 4,097,389 | 6/1978 | Andress, Jr. | 252/51.5 A |
| 4,101,432 | 7/1978 | Okorodudu | 252/49.8 |

Primary Examiner—Andrew Metz
Attorney, Agent, or Firm—Charles A. Huggett; Raymond W. Barclay; Claude E. Setliff

[57] ABSTRACT

The invention provides a lubricant additive having improved antioxidant and antiwear properties made by (1) reacting an alkenylsuccinic anhydride (ASA) with an aminopolyhydroxy compound and (2) reacting the product thus obtained with a phosphorus trihalide and a polyhydroxyaromatic compound. The invention also provides a lubricant composition containing the additive.

12 Claims, No Drawings

LUBRICANT COMPOSITIONS

BACKGROUND OF THE INVENTION

1. Field of the Invention

The invention relates to improving the antiwear and demulsifying properties of a lubricant. More particularly it is concerned with improving such properties by adding to the lubricant a small amount of a phosphorus-containing compound.

2. Description of the Prior Art

Lubricants are subject to heavy stresses that can affect their antioxidant and load carrying ability. Thus, there has been considerable effort to discover classes of compounds that will aid in retaining or, preferably, in improving these important properties.

For example, sulfur compounds have been used for the purpose, as is taught in U.S. Pat. No. 3,697,499. Unfortunately, the presence of sulfur in lubricants may cause severe metal corrosion, especially copper. To overcome this, special processes have been used to moderate the effect of sulfur as in U.S. Pat. No. 3,697,499, or other materials have been used, among them certain phosphorus compounds as lubricant additives. U.S. Pat. No. 3,663,439, for instance, discloses lubricating oils where extreme pressure properties have been improved by adding thereto a reaction product involving a trihydrocarbyl phosphite.

SUMMARY OF THE INVENTION

In accordance with the invention there is provided a lubricant composition comprising lubricant and an antiwear or antioxidant amount of a product made by (1) reacting an alkenylsuccinic anhydride with an aminopolyhydroxy compound and (2) reacting this product with a phosphorus trihalide and a polyhydroxyaromatic compound. The lubricant composition may also contain other additives.

The invention also provides the product per se, i.e., the product of reaction.

DESCRIPTION OF SPECIFIC EMBODIMENTS

Due to the complex nature of the reaction that occurs no precise structure can be applied to the reaction product. Thus, the final product will be referred to herein, both in the specification and claims, as a product of the specified reaction.

The initial reaction product is prepared from primary aminopolyhydroxy compound and alkenylsuccinic anhydride. The aminopolyhydroxy compound may contain from 2 to 20 carbon atoms and from 2 to 4 hydroxyl groups. Illustrative of the useful materials are 1-amino-2,3-dihydroxypropane, 1-amino-2,3,4,-trihydroxybutane, tris(hydroxymethyl)aminomethane, and 1,1-bis(hydroxymethyl)aminomethane and the like. It is further contemplated that the primary aminopolyhydroxy compounds may contain two or more primary amino groups.

The alkenylsuccinic anhydride used in the initial reaction are made by conventional means well-known in the art. The alkenyl portion may contain from 30 to 200 carbon atoms. The alkenyl is added to the anhydride moiety by reacting the appropriate olefin therewith under conditions well-known in the art. The preferred olefins may be prepared by polymerizing, e.g. ethylene, propylene or butylenes using ways known by the art.

The initial product is prepared by reacting at least 1 mole of the anhydride with each mole of the aminopolyhydroxy compound.

In general, the initial reaction can be carried out at from about 120° C. to about 225° C., preferably from about 160° C. to about 185° C. The temperature, of course, is selected in accordance with the amino alcohol and/or anhydride used. Times will vary also depending upon the reactants. These will vary from about 1 hour to about 6 hours and will preferably be from about 1 hour to about 2 hours. The progress of the reaction is monitored by the water formed. Solvents may be used if desired. When used, the solvent should be removed, so it should be selected not only for its ability to solubilize the reactants and the product of reaction, but also for its ease of separation from the reaction medium. When a solvent is not used, it is recommended that any insolubles be removed by filtration or other means.

In the second portion of the reaction outlined, the phosphorus trihalide is preferably phosphorus trichloride, but can be the tribromide or other trihalide. As a general statement, the hydroxyaromatic compound may contain from 6 to 40 carbon atoms and from 2 to 4 hydroxy groups. These include catechol, hydroquinone, resorcinol and the fused ring systems containing 2–4 rings, which ring system may be substituted with a hydrocarbyl group, e.g., an alkyl group, containing up to 34 carbon atoms.

In the preferred practice of the invention, the trihalide and hydroxyaromatic compound are mixed together with the initial reaction product and heated at from about 80° C. to about 175° C., preferably from about 80° C. to about 110° C. Times of reaction will vary from about 1 hour to about 6 hours, preferably from 1 to 2 hours. As in the initial reaction, solvents may be used, with the same precautions mentioned in the general discussion of that reaction. The solvent system may be the same as the one used in the initial reaction, but it may be different.

It is contemplated that the phosphorus trihalide may be reacted with the initial product, followed by reacting this material with the polyhydroxyaromatic compound. When this mode is employed, the conditions disclosed for the mixed reactants are employed.

As has been said, the reaction is extremely complex. In view of this, it is impossible to assign a definite structure to the product. However, while I do not wish to be bound by any structure, I suggest that there may be some product having the following approximate configuration, using a dihydroxyaromatic compound and tris(hydroxymethyl)aminomethane as reactants:

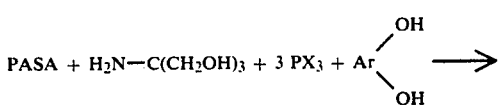

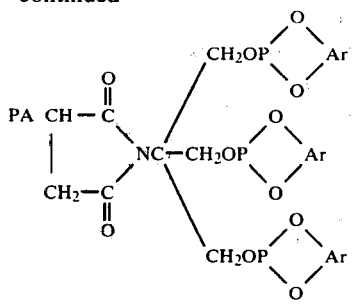

In the second reaction the molar ratio of initial product to PCl₃ and hydroxyaromatic compound will preferably be about 1:3:1. Broadly, such ratios can extend over the range of about 1 to 3:1 to 3:1 to 3.

The lubricants which may be used with the reaction products of this invention are mineral and synthetic lubricating oils and greases therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethylhexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof, (2) 2,2-disubstituted propane diols and (3) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5-C_9$ acids.

As has been indicated, the reaction products disclosed herein are useful as antiwear and antioxidant agents. When so used, they may be added in amounts sufficient to impart such properties to the lubricant. More particularly, such properties will be imparted to the lubricant by adding from about 0.25% to about 10% by weight, preferably from about 1% to about 3%, of the neat product.

Having discussed the invention in broad and general terms, the following are offered to illustrate it. It is to be understood that the examples are merely illustrative and are not intended to limit the scope of the invention.

EXAMPLE

Initial Product

Polybutenyl succinic anhydride 900 SA, obtained from the reaction of equimolecular amounts of maleic anhydride and polybutene at about 200° over a period of 4 hours (100 g., 0.1 mole), toluene (10 ml)—to facilitate the azeotropic removal of the water formed during the condensation reaction—and tris(hydroxymethyl)aminomethane (12.1 g., 0.1 mole) were placed in a flask and heated to 180°–185° under nitrogen with stirring for 2 hours. H₂O (1.8 ml, 0.1 mole) was collected in the attached water trap. The reaction mixture was cooled and toluene (300 ml) was added.

Final Product

The above mixture, containing 110 g. of product, was mixed with 41.2 g. (0.3 mole) of PCl₃ and 33 g. (0.3 mole) of catechol, such that the molar ratio of the respective reactants was 1:3:3. The reaction was carried out at 110° C. for 1 hour, giving 148 g. of product containing 7.29% of phosphorus.

EVALUATION OF PRODUCTS

Various concentrations of the product were tested in 130" solvent paraffinic neutral mineral oil for antioxidant activity. In general, in carrying out this test the antioxidant is added to a solvent-refined mineral lubricating oil. The oil is then heated to 325° F. and dry air at the rate of 5 lit./hr. is passed through it in the presence of iron, copper, aluminum and lead. After 40 hours the neutralization number (NN) for each oil composition is obtained according to ASTM Method D-741-1. The effectiveness of the antioxidants is revealed by comparison of the control of acids (change in neutralization number) with the antioxidant-free oil. The oil employed in accordance with the test results shown in the following table comprise a solvent-refined mineral lubricating oil having a 128/132 SSU viscosity at 100° F. and a 390° F. minimum flash point. The kinematic viscosity change and lead loss are also measured. Table 1 summarizes the results obtained.

TABLE 1

| % by Wt. of Additive | ΔNN | ΔKV.% | Pb Loss |
|---|---|---|---|
| 0.0 | 6.58 | 52.0 | 2.3 |
| 0.5 | 1.14 | 13.6 | 0.0 |
| 1.0 | 1.41 | 13.7 | 0.0 |
| 2.0 | 2.05 | 17.2 | 0.0 |

Shell 4-Ball Test

The products of the Examples were tested in the 4-Ball Test using a modified 4-Ball machine. In this test, three ½" stationary balls (52100 steel) are placed in a lubricant cup and a lubricant containing the additive to be tested is added thereto. A fourth ball is placed on a chuck mounted on a device which can be used to spin the ball at known speeds and loads.

One percent by weight of each product was placed in a blend of a 150" (210° F.) solvent paraffinic bright mineral oil and a 200" (100° F.) solvent paraffinic neutral mineral oil. These were blended in a ratio of 80/20, respectively. The samples were tested at various temperatures and speeds, but always at a load of 60 Kg and for 30 minutes. Table 2 summarizes the test results.

TABLE 2

| Example | Room Temperature | | | | 200° F. | | | | 390° F. | | | |
|---|---|---|---|---|---|---|---|---|---|---|---|---|
| RPM | 500 | 1000 | 1500 | 2000 | 500 | 1000 | 1500 | 2000 | 500 | 1000 | 1500 | 2000 |
| Average Scar Diameter, mm | 0.40 | 0.50 | 0.50 | 0.60 | 0.40 | 0.40 | 0.60 | 0.60 | 0.90 | 1.70 | 0.70 | 2.00 |
| Untreated Oil Average Scar Diameter, mm | | | | | | | | | | | | |

TABLE 2-continued

| Example RPM | Room Temperature | | | | 200° F. | | | | 390° F. | | | |
| --- | --- | --- | --- | --- | --- | --- | --- | --- | --- | --- | --- | --- |
| | 500 | 1000 | 1500 | 2000 | 500 | 1000 | 1500 | 2000 | 500 | 1000 | 1500 | 2000 |
| Final Average | 0.50 | 0.60 | 0.883 | 2.34 | 0.60 | 1.06 | 1.86 | 2.23 | 1.00 | 1.31 | 2.06 | 1.98 |

I claim:

1. A reaction product made by (1) reacting, at from about 120° C. to about 225° C., at least about 1 mole of a polyalkenylsuccinic anhydride with each mole of a primary aminopolyhydroxy compound having from 2 to 20 carbon atoms and from 2 to 4 hydroxyl groups and (2) reacting, at from about 80° C. to about 175° C., the material of (1) with a phosphorus trihalide and a polyhydroxyaromatic compound having from 6 to 40 carbon atoms and from 2 to 4 hydroxyl group, the respective molar ratio being about 1 to 3:1 to 3:1 to 3.

2. The product of claim 1 wherein the polyalkenyl portion of the polyalkenylsuccinic anhydride has a number average molecular weight of about 900.

3. The product of claim 1 wherein said aminopolyhydroxy compound is tris(hydroxymethyl)aminomethane.

4. The product of claim 1 wherein the trihalide is trichloride.

5. The product of claim 1 wherein the polyhydroxyaromatic compound is catechol.

6. A lubricant composition comprising oils of lubricating viscosity or greases thereof and an antioxidant or antiwear amount of the product of claim 1.

7. The composition of claim 6 wherein the polyalkenyl portion has a number average molecular weight of about 900.

8. The composition of claim 6 wherein the said aminopolyhydroxy compound is tris(hydroxymethyl)aminomethane.

9. The composition of claim 6 wherein the trihalide is trichloride.

10. The composition of claim 6 wherein the polyhydroxyaromatic compound is catechol.

11. The product of claim 1 wherein the respective molar ratios are about 1:3:1.

12. The composition of claim 6 wherein the respective molar ratios are about 1:3:1.